US012636245B2

(12) United States Patent
Puppett et al.

(10) Patent No.: US 12,636,245 B2
(45) Date of Patent: May 26, 2026

(54) LIPSTICK

(71) Applicant: Oleon NV, Evergem (BE)

(72) Inventors: Mauro Puppett, Vieux Moulin (FR); Sanggari Mogaraja, Shah Alam (MY); Hilde Peeters, Keerbergen (BE)

(73) Assignee: Oleon NV, Evergem (BE)

(*) Notice: Subject to any disclaimer, the term of this patent is extended or adjusted under 35 U.S.C. 154(b) by 421 days.

(21) Appl. No.: 18/493,075

(22) Filed: Oct. 24, 2023

(65) Prior Publication Data

US 2025/0127703 A1 Apr. 24, 2025

(51) Int. Cl.

*A61K 8/67* (2006.01)
*A61K 8/02* (2006.01)
*A61Q 1/06* (2006.01)

(52) U.S. Cl.

CPC .............. *A61K 8/67* (2013.01); *A61K 8/0229* (2013.01); *A61Q 1/06* (2013.01)

(58) Field of Classification Search

None
See application file for complete search history.

(56) References Cited

FOREIGN PATENT DOCUMENTS

CN 116966102 A * 10/2023

* cited by examiner

*Primary Examiner* — Danah Al-Awadi
(74) *Attorney, Agent, or Firm* — ArentFox Schiff LLP

(57) ABSTRACT

The present invention relates to an improved lipstick, its preparation and a method for improving the hardness, the cutting resistance, and/or the anti-running property of a lipstick.

11 Claims, No Drawings

LIPSTICK

The present invention relates to a lipstick having an improved hardness and/or anti-running/feathering properties, to the process for preparing such a lipstick, and to a method for improving the hardness and/or the anti-running/feathering properties of a lipstick.

Lipsticks have been used for many years to impart color to the lips.

Hardness is one of the main physical properties for lipsticks, as a firm and consistent lipstick will influence its application on the lips. A too hard lipstick will have a poor pay-off and a too soft lipstick will break or not maintain its shape during the application.

The anti-running property or the low feathering property is also an important property, since it prevents feathering or wicking of the product into the skin creases around lips.

Lipsticks are one of the world's most popular cosmetics, with a growing market share.

That is why, many developments are still underway to further improve the properties of lipsticks.

In particular, there is a need for a compound, that would advantageously improve one or all of the following technical effects:

- the hardness of the lipstick;
- the cutting resistance of the lipstick;
- the anti-running property of the lipstick.

The Applicant surprisingly found that a specific emollient could improve the hardness, improve the cutting property, and/or prevent the feathering (anti-running property) of a lipstick.

Accordingly, the present invention relates to a lipstick comprising:

- at least 30% by weight of emollients including at least isocetyl isoarachidol;
- at least 30% by weight of a viscosifying agent;
- at least 0.1% by weight of a coloring agent;
- at least 0.05% by weight of an antioxidant;

wherein the quantity of isocetyl isoarachidol represents at least 10% by weight;

weight percentages being based on the weight of the lipstick.

The lipstick is in a solid form, in particular in the form of a stick.

Isocetyl isoarachidol is a branched alcohol comprising 36 carbon atoms.

Preferably, the quantity of isocetyl isoarachidol is of a least 12% by weight based on the weight of the lipstick.

Preferably, the quantity of isocetyl isoarachidol is of a most 30%, more preferably of at most 25% by weight based on the weight of the lipstick.

Preferably, the quantity of isocetyl isoarachidol is comprised between 10 and 30%, such as between 12 and 30%, more preferably between 12 and 25% by weight based on the weight of the lipstick.

In the present application, unless otherwise indicated, all ranges of values used are to be understood as being inclusive limits.

Preferably, the emollient other than isocetyl isoarachidol is chosen among the group consisting of pentaerythritol tetraisostearate, caprylic/capric triglyceride, triethylhexanoin, vegetable oils such as castor oil, mineral oils, liquid paraffin fractions, tetrahydrofurfuryl alcohols and esters thereof, polyalkylene glycols and their ethers, propylene glycol esters such as propylene glycol monolaurate and propylene glycol monostearate, fatty esters of lower alcohols such as isopropyl myristate, glycerol monostearate and the like, lanolin, petrolatum, and mixtures thereof.

Preferably, the quantity of the emollients, i.e. including the isocetyl isoarachidol, is of at least 35%, more preferably of at least 40% by weight based on the weight of the lipstick.

Preferably, the quantity of the emollients is of a most 65%, more preferably of at most 60%, even more preferably of at most 55% by weight based on the weight of the lipstick.

Preferably, the quantity of the emollients is comprised between 30 and 65%, more preferably between 35 and 60%, even more preferably between 35 and 55% by weight based on the weight of the lipstick By viscosifying agent, it is intended to mean a compound that increases the viscosity or stiffens without hardening the composition where it is used.

Preferably, the viscosifying agent is chosen among the group consisting of waxes; organophilic clays; silica; alkyl guar gums; silicone-based resins; maltodextrin; starch; fatty alcohols and their esters, such as cetearyl alcohol, cetyl alcohol, stearyl alcohol, palmitic alcohol, cetyl palmitate, triisostearin, myristyl myristate and myristyl stearate; botanical derived butters, such as butyrospermum parkii butter (shea butter), mango butter, mango seed butter, raspberry butter, avocado butter, olive butter, kuku butter, monoi butter, peach butter, pistachio butter, coconut butter, cocoa butter, pomegranate butter, rose hip butter, sunflower butter, wheat germ butter, apricot butter, babassu butter, cupuacu butter, kokum butter, hazelnut butter, jojoba butter, sesame butter, soy butter, almond butter, meadowfoam seed butter, black current seed butter and cranberry butter; and mixtures thereof.

The waxes may be of natural origin, for instance beeswax, carnauba wax, candelilla wax, ouricoury wax, Japan wax, cork fiber wax or sugar cane wax, paraffin wax, lignite wax, microcrystalline waxes, lanolin wax, montan wax, ozokerites, and hydrogenated oils such as hydrogenated jojoba oil.

The waxes may be of synthetic origin, for instance polyethylene waxes derived from the polymerization of ethylene, waxes obtained by Fischer-Tropsch synthesis, esters of fatty acids and of glycerides that are solid at 40° C. at atmospheric pressure.

Preferably, the wax is selected among the group consisting of *Oryza Sativa* Bran (rice bran) Wax, *Euphorbia Cerifera* (Candelilla) Wax, *Cera Alba* (beeswax), and mixtures thereof.

More preferably, the viscosifying agent is chosen among the group consisting of waxes; alkyl guar gums; maltodextrin; starch; botanical derived butters, such as butyrospermum parkii butter (shea butter), Mango butter, mango seed butter, raspberry butter, avocado butter, olive butter, kuku butter, monoi butter, peach butter, pistachio butter, coconut butter, cocoa butter, pomegranate butter, rose hip butter, sunflower butter, wheat germ butter, apricot butter, babassu butter, cupuacu butter, kokum butter, hazelnut butter, jojoba butter, sesame butter, soy butter, almond butter, meadowfoam seed butter, black current seed butter and cranberry butter; cetearyl alcohol; cetyl alcohol; stearyl alcohol; palmitic alcohol; cetyl palmitate; myristyl myristate; myristyl stearate; and mixtures thereof.

Preferably, the quantity of the viscosifying agent is of at least 35%, more preferably of at least 40% by weight based on the weight of the lipstick.

Preferably, the quantity of the viscosifying agent is of a most 65%, more preferably of at least 60% by weight based on the weight of the lipstick.

Preferably, the quantity of the viscosifying agent is comprised between 30 and 65%, more preferably between 35 and 65%, even more preferably between 40 and 60% by weight based on the weight of the lipstick.

The coloring agent is preferably chosen among coloring agents usually used in the field of cosmetics.

The coloring agent is preferably chosen among the group consisting of pigments, such as mineral and organic pigments; dyes; and mixtures thereof.

A pigment is a natural or synthetic substances that is intended for colouring and/or opacifying.

The pigment may be chosen among pigments usually used in the field of cosmetics.

Each pigment may be white or colored, mineral or organic, coated or uncoated and of usual or nanometric size.

Examples of mineral pigments are titanium dioxide; iron oxides, such as iron trioxide, iron tetraoxide; mica; zinc oxide; chromium oxides, such as dichromium trioxide; barium sulphate, aluminium hydroxide, silver, magnesium carbonate, zirconium oxide, cerium oxide, manganese violet, ultramarine blue, chromium hydrate; and ferric blue.

Examples of organic pigments are carbon black, pigments of D&C type, and lakes based on cochineal carmine or on barium, strontium, calcium or aluminium.

The pigments may be coated with one silicone compound such as polydimethylsiloxanes; one polymer, especially polyethylenes; one fluoro compound; and/or one amino acid. Mention may also be made of "SI oxides" which are polymethyl-hydrogenosiloxane-coated pigment.

Pearlescent pigments are pigments that have been coated with another mineral or organic pigment. The pearlescent pigments may be white, such as mica coated with titanium dioxide or with bismuth oxychloride; or coloured, such as mica coated with iron oxides, mica coated with titanium dioxide and ferric blue or chromium oxide, mica coated with an organic pigment of the abovementioned type.

A dye is an organic substance which may be natural or synthetic.

The dye is preferably chosen among dyes usually used in the field of cosmetics, such as red dyes CI 15850 (Red 6 Lake) and CI 45410 (Red 28 Lake).

Preferably, the quantity of the coloring agent is of at least 0.5%, more preferably of at least 1%, even more preferably of at least 2% by weight based on the weight of the lipstick.

Preferably, the quantity of the coloring agent is of a most 30%, more preferably of at most 25% by weight based on the weight of the lipstick.

Preferably, the quantity of the coloring agent is comprised between 1 and 30%, more preferably between 2 and 25%, even more preferably between 2 and 20%, by weight based on the weight of the lipstick.

Preferably, the lipstick comprises a mixture of coloring agents, in particular a mixture of pigments.

The antioxidant may be chosen among antioxidants usually used in the field of cosmetics.

Examples of antioxidant are acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

Preferably, the quantity of the antioxidant is of at least 0.1%, more preferably of at least 0.15%, even more preferably of at least 0.2% by weight based on the weight of the lipstick.

Preferably, the quantity of the antioxidant is of a most 1%, more preferably of at most 0.8% by weight based on the weight of the lipstick.

Preferably, the quantity of the antioxidant is comprised between 0.05 and 1%, more preferably between 0.1 and 1%, such as between 0.15 and 1%; even more preferably between 0.2 and 0.8 by weight based on the weight of the lipstick.

Advantageously, the lipstick according to the invention, comprises:

- 30-65% by weight of emollients including at least isocetyl isoarachidol;
- 30-65% by weight of a viscosifying agent;
- 0.1-30% by weight of a coloring agent;
- 0.05-1% by weight of an antioxidant;

wherein the quantity of isocetyl isoarachidol represents between 10 and 30% by weight;

weight percentages being based on the weight of the lipstick.

Advantageously, the lipstick according to the invention, further comprises a flavoring agent and/or an organic UV filter.

Examples of flavoring agents that may be added in the lipstick according to the invention are cosmetic blends designed by the INCI Aroma or a sweetener such as glycyrrhizin and its salts, erythritol, *Stevia Rebaudiana* Extract, sugar.

Preferably, the quantity of the flavoring agent is of at least 0.1%, more preferably of at least 0.2% by weight based on the weight of the lipstick.

Preferably, the quantity of the flavoring agent is of a most 1%, more preferably of at most 0.8% by weight based on the weight of the lipstick.

Preferably, the quantity of the flavoring agent is comprised between 0.1 and 1%, more preferably, between 0.2 and 0.8% by weight based on the weight of the lipstick Examples of organic UV filters that may be added in the lipstick according to the invention are ethylhexyl methoxycinnamate, octocrylene, butyl methoxydibenzoylmethane, benzophenone-3, diethylamino hydroxybenzoyl hexyl benzoate, bis-ethylhexyloxyphenol methoxyphenyl triazine and ethylhexyl triazone.

Preferably, the quantity of the organic UV filter is of at least 0.1%, more preferably, of at least 0.5% by weight based on the weight of the lipstick.

Preferably, the quantity of the organic UV filter is of a most 30%, more preferably, of at most 25%, even more preferably of at most 22.8% by weight based on the weight of the lipstick.

Preferably, the quantity of the organic UV filter is comprised between 0.1 and 30%, more preferably, between 0.5 and 25% by weight based on the weight of the lipstick A particularly preferred lipstick according to the invention comprises:

- 35-55% by weight of emollients including at least isocetyl isoarachidol;
- 40-60% by weight of a viscosifying agent;

2-25% by weight of a coloring agent;

0.2-0.8% by weight of an antioxidant;

optionally 0.1-1% of a flavoring agent;

optionally 0.1-22.8% by weight of an organic UV filter;

wherein the quantity of isocetyl isoarachidol represents from 10 to 30% by weight;

weight percentages being based on the weight of the lipstick.

The lipstick may further comprise an active agent other than antioxidant. This active agent may comprise a compound having a cosmetic and/or dermatological effect, especially on the lips. This active ingredient may be hydrophobic or hydrophilic and may be chosen among the group consisting of skin-relaxing agents, agents stimulating the synthesis of dermal or epidermal macromolecules and/or preventing their degradation, anti-glycation agents, anti-irritants, hydrating agents such as polyhydric alcohols and water-soluble alkoxylated non-ionic polymers, desquamating agents, pigmentation modifying agents, NO-synthase inhibitors, fibroblast proliferation stimulating agents or keratinocytes and/or the differentiation of keratinocytes, anti-pollution or anti-radical agents, soothing agents, agents acting on the microcirculation, agents acting on the energetic metabolism of cells, healing agents, and mixtures thereof.

The quantity of the active agent other than antioxidant may be up to 5% by weight based on the weight of the lipstick.

The lipstick may also comprise a preservative and/or wetting agent.

More particularly, the preservative is chosen among the group consisting of phenoxyethanol, glycol ethers, benzoic acid, sorbic acid, salicylic acid, glycols, parabens, thiazolinones, ethylhexylglycerin, aldehydes; and mixtures thereof.

Preferably, the wetting agent is polyglyceryl-3 diisostearate.

Preferably, the lipstick is free of water.

More particularly, the lipstick comprise less than 1% by weight, preferably less than 0.5% by weight of water, more preferably no water.

In a first aspect, the present invention provides a lipstick which does not comprise an oil gelling agent selected from the group consisting of dextrin fatty acid esters, polysaccharide fatty acid esters, clay minerals modified with organic compounds, 12-hydroxystearic acid, and alkyl glutamides, such as dibutyl ethylhexanoyl glutamide and dibutyl lauroyl glutamide.

In a second aspect, the present invention provides a lipstick which does not comprise ethyl cellulose polymer.

An ethyl cellulose polymer is a derivative of cellulose, wherein some hydroxyl groups on the repeating glucose units are converted into ethoxyl groups. In particular, the ethyl cellulose polymer is of formula (I):

(I)

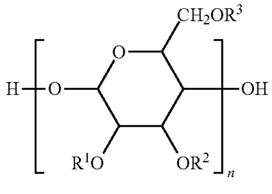

wherein $R^1$, $R^2$ and $R^3$, identical or different, represent H or $CH_2CH_3$, and n, an integer, is of at least 2.

In a third aspect, the present invention provides a lipstick which does not comprise a dimer diol.

A dimer diol is a mixture of cyclic and noncyclic isomers, known by the skilled person. A dimer diol is usually obtained by:

dimerization of unsaturated fatty acid(s) or ester(s) thereof followed by reduction of respectively acid or ester groups into hydroxyl groups, or dimerization of unsaturated fatty alcohol(s).

Preferably, unsaturated fatty acid(s) or ester(s) thereof and unsaturated fatty alcohol(s) are respectively mono carboxylic acid(s) or ester(s) and mono alcohol(s), each hydrocarbon chain of fatty acid(s) or fatty alcohol(s) comprising between 18 and 24, preferably between 18 and 22 carbon atoms. Also, dimer diol molecules preferably comprise between 36 and 48, more preferably between 36 and 44 carbon atoms, such as 36 carbon atoms.

In particular, the dimer diol is prepared from unsaturated fatty acid(s) or unsaturated fatty alcohol(s) comprising 18 carbon atoms Preferably, the dimer diol comprises more than 50% by weight, more preferably more than 70% by weight of noncyclic isomers, percentages by weight being given on the total weight of the dimer diol. By total weight of the dimer diol, it is intended the weight of all dimer diol molecules.

In a fourth aspect, the present invention provides a lipstick which comprises neither an oil gelling agent selected from the group consisting of dextrin fatty acid esters, polysaccharide fatty acid esters, clay minerals modified with organic compounds, 12-hydroxystearic acid, and alkyl glutamides, such as dibutyl ethylhexanoyl glutamide and dibutyl lauroyl glutamide; nor ethyl cellulose polymer.

In a fifth aspect, the present invention provides a lipstick which comprises neither dimer diol nor ethyl cellulose polymer.

In a sixth aspect, the present invention provides a lipstick which comprises neither an oil gelling agent selected from the group consisting of dextrin fatty acid esters, polysaccharide fatty acid esters, clay minerals modified with organic compounds, 12-hydroxystearic acid, and alkyl glutamides, such as dibutyl ethylhexanoyl glutamide and dibutyl lauroyl glutamide; dimer diol; nor ethyl cellulose polymer.

Preferably, the lipsticks according to the invention present improved hardness, and cutting property and/or anti-running property.

More preferably, the lipsticks according to the invention present improved hardness, improved cutting property and anti-running property.

The present invention also relates to a process for preparing a lipstick according to the invention, comprising the following steps:

i) mixing a phase A with a phase B;

wherein the phase A comprises a viscosifying agent and an emollient; and wherein the phase B comprises a coloring agent dispersed in isocetyl isoarachidol; and ii) adding a phase C to the mixture resulting from step i); wherein the phase C comprises an antioxidant.

The coloring agent of phase B is dispersed within isocetyl isoarachidol prior to the mixing with the phase A. In particular, phase B can be passed through a tricylinder.

Preferably, the phase A is heated until the compounds melted.

Advantageously, in the process for preparing a lipstick according to the invention, the phase A is heated at a temperature of at least 40° C., before mixing.

Preferably, the phase A is heated at a temperature of at least 60° C., more preferably of at least 80° C.

Preferably, in the step ii), the addition is carried out under mixing.

Advantageously, in the process for preparing a lipstick according to the invention, the step ii) is carried out at a temperature of at least 40° C.

Preferably, the step ii) is carried out at a temperature of at least 50° C., such as 60° C.

Advantageously, the process for preparing a lipstick according to the invention, further comprises a step of forming the lipstick.

Preferably, in the step of forming the lipstick, the resulting mixture of step ii) is poured into a lipstick mold.

The resulting mixture is at a temperature of at least 40° C., more preferably of at least 50° C., even more preferably of at least 60° C.

Then, the resulting mixture is allowed to cooled down, preferably until the resulting mixture reach a temperature between 2° and 30° C.

The formed lipstick may be then unmolded.

The present invention also concerns a method for improving the hardness, the cutting resistance, and/or the anti-running property of a lipstick, comprising the use of at least 10% by weight of isocetyl isoarachidol in the formulation of said lipstick, weight percentage being based on the weight of the lipstick.

The isocetyl isoarachidol and the lipstick are as described above, including preferential and advantageous features.

More particularly, the Example 2.1 shows that the substitution of 20% by weight of an emollient or a viscosifying agent by isocetyl isoarachidol in the formulation of a lipstick, weight percentage being based on the weight of the lipstick, leads to a lipstick with improved hardness.

The increase of the hardness of the lipstick by substituting an emollient or a viscosifying agent by isocetyl isoarachidol is preferably of at least 10%, more preferably of at least 15%, even more preferably of at least 20%.

Example 2.2 shows that the substitution of 20% by weight of an emollient by isocetyl isoarachidol in the formulation of a lipstick, weight percentage being based on the weight of the lipstick, leads to a lipstick with improved the cutting property.

The improvement of the cutting resistance of a lipstick by substituting an emollient or a viscosifying agent by isocetyl isoarachidol is preferably of at least 10%, more preferably of at least 15%, even more preferably of at least 20%.

Example 2.3 shows that the substitution of 20% by weight of an emollient by isocetyl isoarachidol in the formulation of a lipstick, weight percentage being based on the weight of the lipstick, lead to a lipstick with improved anti-running property.

The improvement of the anti-running property of a lipstick is characterized by a decrease of the spreading area of the pigments of the lipstick by at least 10%, preferably by at least 15%, more preferably by at least 20%, by substituting an emollient or a viscosifying agent by isocetyl isoarachidol.

Advantageously, in the method according to the invention, the lipstick comprises:

- 20-55% by weight of emollients other than isocetyl isoarachidol;
- 30-65% by weight of a viscosifying agent;
- 0.1-30% by weight of a coloring agent;
- 0.05-1% by weight of an antioxidant;
- optionally 0.1-1 of a flavouring agent;
- optionally 0.1-22.8% by weight of an organic UV filter;

weight percentages being based on the weight of the lipstick.

The invention is further described in the following examples, given by way of illustration.

Chemicals Used in Examples

Emollients:
- isocetyl isoarachidol: Radiastar 1436 from Oleon;
- C12-15 alkyl benzoate: Finsolv TN from Innospec;
- octydodecanol: Radiastar 1420 from Oleon
- caprylic/capric triglyceride: Radia 7104 from Oleon;
- triethylhexanoin: Radia 7610 from Oleon;
- pentaerythritol tetraisostearate: Jolee 7181 from Oleon;

Viscosifying agents:
- *Oryza Sativa* Bran (Rice Bran) Wax from Kerfoot;
- *Euphorbia Cerifera* (Candellila) Wax: Candelilla wax from Kerfoot;
- *Cera Alba*: Beeswax organic from Kerfoot;
- myristyl myristate: Radia 7744 from Oleon;
- cetearyl alcohol: Ecorol 68/30 from Ecogreen;
- cetyl palmitate: Radia 7500 from Oleon
- butyrospermum parkii butter (shea butter) from Kerfoot;
- triisostearin: Radia 7373 from Oleon;

Wetting agent:
- polyglyceryl-3 diisostearate: Jolee 7245 from Oleon;

Coloring agents:
- white:
- CI 77891 (titanium dioxide): Kronos 1171 (average particle size: 136.8-140.8 nm) from Kronos;
- red:
- CI 45410 (Red 28): Unipure Red LC328 from Sensient Beauty;
- CI 77491 (iron dioxide) and jojoba esters: BRO-NJE2 from Kobo;
- CI 77019 (mica), CI 77891 and CI 77491: KT-6213 from Kolortek;
- CI 15850 (Red 6): Unipure Red LC304 from Sensient Beauty;

Liquid organic UV filter:
- ethylhexyl methoxycinnamate: Eusolex 2292 from Merck;

Antioxidant:
- Tocopheryl acetate: vitamin E from BASF;

Flavoring agent:
- Aroma: strawberry emulco from Green House Ingredients.

EXAMPLE 1: LIPSTICKS 1.1 Lipstick L1

Chemicals and their quantities are described in Table 1 below.

This lipstick was prepared according to the following steps:

Phase A was prepared by introducing the corresponding ingredients into the main beaker under stirring until good homogenization.

Phase A was then heated to 80° C. until melted.

Phase B was prepared by introducing the corresponding ingredients in a separate beaker under stirring until homogeneous. Phase B was then passed to trycilinder three times.

Phase B was added to phase A under stirring at 60° C.

Phase C was prepared by mixing the corresponding ingredients together at room temperature.

Phase C was then added to the mixture of phases A and B under stirring until homogeneous at 60° C.

Then, the formulation was poured into the mold and cooled down at room temperature before unmolding.

TABLE 1

Formulations of the lipstick L1 according to the invention and of the comparative lipsticks CL1-CL2

| | INCI names | Function | Lipstick L1 (% w/w) | Comparative lipstick CL1 (% w/w) | Comparative lipstick CL2 (% w/w) |
|---|---|---|---|---|---|
| A | *Euphorbia Cerifera* (Candellila) Wax | viscosifying agent | 15.7 | 15.7 | 15.7 |
| | *Oryza Sativa* Bran (Rice Bran)Wax) | viscosifying agent | 14.8 | 14.8 | 14.8 |
| | Cera Alba | viscosifying agent | 3.8 | 3.8 | 3.8 |
| | Myristyl myristate | viscosifying agent | 4.6 | 4.6 | 4.6 |
| | *Butyrospermum Parkii* | viscosifying agent | 2.8 | 2.8 | 2.8 |
| | Triethylhexanoin | emollient | 12.8 | 12.8 | 12.8 |
| | Caprylic/capric triglyceride | emollient | 12.8 | 12.8 | 12.8 |
| | Cetearyl alcohol | viscosifying agent | 4.6 | 4.6 | 4.6 |
| B | Isocetyl isoarachidol | emollient | 20.0 | | |
| | C12-15 alkyl benzoate | emollient | | 20.0 | |
| | octyldodecanol | emollient | | | 20.0 |
| | CI 77891 | pigment | 1.8 | 1.8 | 1.8 |
| | CI 15850 | dye | 1.5 | 1.5 | 1.5 |
| | CI 45410 | pigment | 1.5 | 1.5 | 1.5 |
| | CI 77491 and jojoba esters | pigment | 1.0 | 1.0 | 1.0 |
| | Mica, CI 77891 and CI 77491 | pearlescent pigment | 0.2 | 0.2 | 0.2 |
| C | Ethylhexyl methoxycinnamate | UV filter | 1.4 | 1.4 | 1.4 |
| | Tocopheryl acetate | antioxidant | 0.2 | 0.2 | 0.2 |
| | Aroma | flavoring agent | 0.5 | 0.5 | 0.5 |

1.2 Lipstick L2

Chemicals and their quantities are described in Table 2 below.

This lipstick was prepared according to the method described in Example 1.1.

TABLE 2

Formulations of the lipstick L2 according to the invention and of the comparative lipsticks CL3-CL4

| | INCI names | Function | Lipstick L2 (% w/w) | Comparative lipstick CL3 (% w/w) | Comparative lipstick CL4 (% w/w) |
|---|---|---|---|---|---|
| A | *Oryza Sativa* Bran (Rice Bran) Wax | viscosifying agent | 12 | 12 | 12 |
| | Cetyl palmitate | viscosifying agent | 10 | 10 | 10 |
| | Myristyl myristate | viscosifying agent | 2 | 2 | 2 |
| | Cetearyl alcohol | viscosifying agent | 2 | 2 | 2 |
| | Polyglyceryl-3 diisostearate | wetting agent | 2 | 2 | 2 |
| | *Butyrospermum Parkii* | viscosifying agent | 1 | 1 | 1 |
| | Pentaerythritol tetraisostearate | emollient | 18 | 18 | 18 |
| B | Isocetyl isoarachidol | emollient | 20 | | |
| | Triisostearin | viscosifying agent | 15 | 35 | 15 |
| | octyldodecanol | emollient | | | 20 |
| | Caprylic/capric triglyceride | emollient | 13.5 | 13.5 | 13.5 |

TABLE 2-continued

| Formulations of the lipstick L2 according to the invention and of the comparative lipsticks CL3-CL4 | | | | | |
|---|---|---|---|---|---|
| | INCI names | Function | Lipstick L2 (% w/w) | Comparative lipstick CL3 (% w/w) | Comparative lipstick CL4 (% w/w) |
| | CI 77891 | pigment | 2 | 2 | 2 |
| | CI 15850 | dye | 1 | 1 | 1 |
| | CI 45410 | pigment | 1 | 1 | 1 |
| C | Tocopheryl acetate | antioxidant | 0.5 | 0.5 | 0.5 |

EXAMPLE 2: CHARACTERISTICS OF THE LIPSTICKS

2.1 Hardness

The hardness is a measure of the resistance of a material, here a lipstick, to the penetration of an external body, here a cylinder probe.

The hardness was measured with a Lloyd Instruments/Ametek TA1 Texture Analyzer and the Nexygen Plus V3 software, using the following characteristics: probe cylinder with diameter of 12 mm, area of probe of 113.1 $mm^2$, preload of 0.2 N (zero point), speed of going to zero point of 100 mm/min, speed during measurement of 20 mm/min, depth of 5 mm, force max of 50 N and temperature of 22° C.

Results are given in Table 3 below.

TABLE 3

| Hardness of lipsticks | |
|---|---|
| | Hardness (N) |
| Lipstick L1 | 1.78 |
| Comparative lipstick CL1 | 1.26 |
| Comparative lipstick CL2 | 1.01 |
| Lipstick L2 | 0.45 |
| Comparative lipstick CL3 | 0.27 |
| Comparative lipstick CL4 | 0.37 |

Hardness values obtained with lipsticks according to the invention (L1 and L2) are higher than hardness values of respective comparative lipsticks (CL1 and CL2 for L1; and CL3 and CL4 for L2), which means that isocetyl isoarachidol makes it possible to improve the hardness of a lipstick without adding more wax.

The lipsticks L1 and L2 present good hardness and are hard enough to allow the distribution of the product on the lips, without breaking.

With lower values of hardness, L2 is a creamier texture.

2.2 Cutting resistance average force

The cutting resistance average force is a test to assess the firmness of a lipstick based on the resistance force opposed by the stick to the penetration of a cutting wire probe.

It was measured with a Lloyd Instruments/Ametek TA1 Texture Analyzer and the Nexygen Plus V3 software, using the following characteristics: wire probe with diameter of 0.3 mm, preload of 0.2 N (zero point), speed of going to zero point of 100 mm/min, speed during measurement of 20 mm/min, depth of 5 mm, force max of 50 N and temperature of 22° C.

The diameter of the lipsticks were around 1.3 cm.

Results are given in Table 4 below.

TABLE 4

| Cutting resistance average force of lipsticks | |
|---|---|
| | Cutting resistance average force (N) |
| Lipstick L1 | 8.48 |
| Comparative lipstick CL1 | 6.88 |
| Comparative lipstick CL2 | 6.88 |
| Lipstick L2 | 1.42 |
| Comparative lipstick CL3 | 0.88 |
| Comparative lipstick CL4 | 1.19 |

Cutting resistance average force values obtained with lipsticks according to the invention are higher than the cutting resistance average force values of respective comparative lipsticks, which means that isocetyl isoarachidol makes it possible to improve the cutting resistance of a lipstick without adding more wax.

The lipsticks L1 and L2 present good cutting resistance, meaning the lipsticks according to the invention will not break during normal handling. Especially during the sliding movement when the lipstick is inserted in or extracted from its plastic tube could make it break against the border of the tube.

2.3 Anti-Running

The anti-running property of a lipstick refers to the spreading of the pigments into the fine lines around the lips, which can cause a loss of definition of the line designed, when a lipstick is applied to the lips. It also means that smudging is reduced.

The anti-running property of each lipstick was measured by a spreading test, applying the product on a sheet of paper, within a defined surface of 50.0 mm and measuring the final diameter, after 20 min at 37° C.

Results, given in Table 5 below, are expressed as the percentage of difference between initial and final diameters.

TABLE 5

| Anti-running of lipsticks | |
|---|---|
| | % of difference of initial and final areas |
| Lipstick L2 | 35 |
| Comparative lipstick CL3 | 73 |
| Comparative lipstick CL4 | 48 |

It can be observed that the lipstick L2 presents the lowest percentage difference between areas compared to other lipsticks CI3-CL4 comprising no isocetyl isoarachidol. It can be concluded that the presence of isocetyl isoarachidol in a lipstick improves the anti-running property of the lipstick.

2.4 Glossiness

The glossiness of lipstick was measured with a Glossymeter GL200 Probe for MDD4 by Courage Kazaka.

Results are given in Table 6 below.

TABLE 6

| Average glossiness of lipsticks | |
|---|---|
| | Average glossiness (GU) |
| Lipstick L1 | 9.34 |
| Comparative lipstick CL1 | 9.84 |
| Comparative lipstick CL2 | 5.83 |
| Lipstick L2 | 17.38 |
| Comparative lipstick CL3 | 4.52 |
| Comparative lipstick CL4 | 9.93 |

All lipsticks present a good glossiness property.

The average glossiness values obtained with lipsticks according to the invention are similar or higher than the average glossiness values of comparative lipsticks, which means that isocetyl isoarachidol makes it possible to improve the glossiness of a lipstick.

The invention claimed is:

1. A lipstick comprising:

at least 30% by weight of emollients including at least isocetyl isoarachidol;

at least 30% by weight of a viscosifying agent;

at least 0.1% by weight of a coloring agent; and at least 0.05% by weight of an antioxidant;

wherein the quantity of isocetyl isoarachidol represents at least 10% by weight; weight percentages being based on the weight of the lipstick.

2. The lipstick according to claim 1, comprising:

30-65% by weight of emollients including at least isocetyl isoarachidol;

30-65% by weight of a viscosifying agent;

0.1-30% by weight of a coloring agent; and 0.05-1% by weight of an antioxidant;

wherein the quantity of isocetyl isoarachidol represents between 10 and 30% by weight; weight percentages being based on the weight of the lipstick.

3. The lipstick according to claim 1, further comprising a flavoring agent and/or an organic UV filter.

4. A process for preparing a lipstick according to claim 1, comprising the following steps of:

i) mixing a phase A with a phase B;

wherein the phase A comprises a viscosifying agent and an emollient; and wherein the phase B comprises a coloring agent dispersed in isocetyl isoarachidol; and ii) adding a phase C to the mixture resulting from step i);

wherein the phase C comprises an antioxidant.

5. The process for preparing a lipstick according to claim 4, wherein the phase A is heated at a temperature of at least 40° C., before mixing.

6. The process for preparing a lipstick according to claim 4, wherein the step ii) is carried out at a temperature of at least 40° C.

7. The process for preparing a lipstick according to claim 4, further comprising a step of forming the lipstick.

8. A method for improving the hardness, the cutting resistance, and/or the anti-running property of a lipstick, comprising the use of at least 10% by weight of isocetyl isoarachidol in the formulation of said lipstick, weight percentage being based on the weight of the lipstick.

9. The method according to claim 8, wherein the lipstick comprises:

20-55% by weight of emollients other than isocetyl isoarachidol;

30-65% by weight of a viscosifying agent;

0.1-30% by weight of a coloring agent;

0.05-1% by weight of an antioxidant;

optionally 0.1-1% of a flavoring agent; and optionally 0.1-22.8% by weight of an UV filter;

weight percentages being based on the weight of the lipstick.

10. The lipstick according to claim 2, further comprising a flavoring agent and/or an organic UV filter.

11. The process for preparing a lipstick according to claim 5, wherein the step ii) is carried out at a temperature of at least 40° C.

* * * * *